United States Patent
Jaeger et al.

(10) Patent No.: US 6,838,100 B2
(45) Date of Patent: Jan. 4, 2005

(54) CULTURED PROTEIN HYDROLYSATE

(75) Inventors: Daniel Jaeger, Hagenbuch (CH); Cristina Hering-Giovanola, Breganzona (CH); Michael Affolter, Savigny (CH)

(73) Assignee: Givaudan S.A., Vernier (CH)

( * ) Notice: Subject to any disclaimer, the term of this patent is extended or adjusted under 35 U.S.C. 154(b) by 0 days.

(21) Appl. No.: 10/229,687

(22) Filed: Aug. 27, 2002

(65) Prior Publication Data

US 2003/0113403 A1 Jun. 19, 2003

Related U.S. Application Data

(63) Continuation of application No. PCT/EP01/03807, filed on Apr. 3, 2001.

(30) Foreign Application Priority Data

Apr. 7, 2000 (EP) .............................. 00201274

(51) Int. Cl.$^7$ ................................ A23L 1/00
(52) U.S. Cl. .......................... 426/52; 426/42; 426/49; 426/56; 426/589; 426/650; 435/252.1; 435/252.9
(58) Field of Search .............. 426/34, 42, 43, 426/49, 52, 55, 56, 589, 650; 435/252.1, 252.9

(56) References Cited

U.S. PATENT DOCUMENTS

| | | | | |
|---|---|---|---|---|
| 3,852,479 A | | 12/1974 | Yokotsuka et al. | 426/44 |
| 3,912,822 A | | 10/1975 | Yokotsuka et al. | 426/44 |
| 4,001,437 A | | 1/1977 | Jaeggi et al. | 426/34 |
| 5,147,667 A | | 9/1992 | Kwon et al. | 426/56 |
| 5,965,178 A | | 10/1999 | Baensch et al. | 426/52 |
| 6,569,476 B2 | * | 5/2003 | Lim et al. | 426/46 |

FOREIGN PATENT DOCUMENTS

| | | |
|---|---|---|
| EP | 505 733 A1 | 9/1992 |
| JP | 05049385 A | 3/1993 |
| JP | 07147898 A | 3/1993 |

* cited by examiner

Primary Examiner—Leslie Wong
(74) Attorney, Agent, or Firm—Winston & Strawn

(57) ABSTRACT

This invention relates to a process for the production of a cultured savory base by hydrolyzing a protein-containing material using a combination of at least one enzyme with at least one thermotolerant lactic acid bacteria strain selected for its ability to provide a glutaminase activity. The invention also relates to an isolated strain of thermotolerant lactic acid bacteria strains selected for their ability to provide a glutaminase activity and their use for preparing a seasoning or flavor for culinary or petfood products.

19 Claims, No Drawings

CULTURED PROTEIN HYDROLYSATE

CROSS-REFERENCE TO RELATED APPLICATIONS

This application is a continuation of the U.S. national stage designation of International application PCT/EP01/03807 filed Apr. 3, 2001, the entire content of which is expressly incorporated herein by reference thereto.

FIELD OF THE INVENTION

This invention relates to a process for the production of a cultured savory base wherein a protein-containing material is hydrolyzed by the combination of enzymes with at least one thermotolerant lactic acid bacteria strain selected for its ability to provide a glutaminase activity. The invention also relates to novel thermotolerant lactic acid bacteria strains selected for their ability to provide a glutaminase activity and their use in liquid seasoning, culinary product and process flavor.

BACKGROUND OF THE INVENTION

Hydrolyzed proteins have been known for use as seasonings in the form of soya sauce, which traditionally has been prepared by enzymatic hydrolysis requiring a long period of time for preparation. In producing soya sauce, plant protein-containing materials and carbohydrates are inoculated with *Aspergilli* and the solid culture is fermented for 2 days to make koji, during this time enzymes are produced which are able to hydrolyze protein and carbohydrates in the moromi stage. The koji is mixed with a solution of common salt and water to give moromi, which is fermented for 4 weeks to 8 months by the activity of micro-organisms such as soya lactic acid bacteria and soya yeast, and the soya sauce is obtained by removing the solids portion from the fermented moromi.

A more rapid method of hydrolyzing proteins for producing seasonings was developed using hydrochloric acid in which the time required is only a few hours. However, the use of acid hydrolyzed plant protein (HPP) in culinary applications came under attack due to mono- and di-chloropropanols which were formed during the harsh processing conditions.

More recently, several processes were developed to replace HPP. Thus, in U.S. Pat. No. 5,523,100 a seasoning agent is prepared on modified standard soya sauce technology. In this process the koji is treated before forming the moromi, by a low hydrolysis temperature whereby the resultant seasoning has a stronger body than a standard soya sauce.

Biological plant protein hydrolysates which are used as neutral body givers in liquid seasonings, culinary applications and as bases for processed flavors like bouillons, soups and sauces, are also developed.

In U.S. Pat. No. 5,965,178, Baensch et al. disclose a process for the production of a seasoning which comprises preparing a fermented koji from protein-containing and carbohydrate materials and then hydrolyzing the koji material in the presence of a culture of lactic acid bacteria. The seasoning composition is obtained without preparing a moromi.

The problem is that biological hydrolysates are generally more expensive to produce than HPP due to lower yields, higher equipment costs and higher raw material prices e.g. enzymes (commercial or own production by fermentation).

Finally, it is also known to hydrolyze wheat gluten enzymatically using commercially available enzymes. The critical points in the development of WGH-te (Wheat Gluten Hydrolysate—technical enzymes) processes are mainly the high costs of these enzymes, separation of solids from the hydrolysates with high yield and microbiological protection of the hydrolysates since they are run without or low salt concentrations, at temperatures permissible for certain spoilage micro-organisms.

The present invention aims to provide a natural and "soft technology" procedure to prepare seasonings, which is very much desired by consumers these days.

SUMMARY OF THE INVENTION

Surprisingly, it has been found that some lactic acid bacteria (LAB) strains used in combination with enzymes may have a synergistic activity in producing savory bases which are good body givers and contain significant amounts of "in process produced" mono sodium glutamate or glutamic acid. In the present specification, MSG is used to refer either to mono sodium glutamate or glutamic acid.

Accordingly, this invention provides a process for the production of a cultured savory base which comprises hydrolyzing a protein-containing material using a combination of at least one enzyme with at least one thermotolerant LAB strain selected for its ability to provide a glutaminase activity.

In a preferred embodiment, the enzyme is any technical endo- or exo-peptidase and/or protease, deaminase, transaminase or amyloglucosidase, for example.

In a preferred embodiment, the LAB is used in the form of a starter (innoculum). The LAB may be selected from the group consisting of facultative heterofermentative *Lactobacilli*, *Lactobacillus rhamnosus*, *Lactobacillus delbrucki*, *Lactobacillus casei*, *Lactobacillus paracasei*, and *Lactobacillus* sp. In a most preferred embodiment, the LAB strain is *Lactobacillus rhamnosus* (NCC 858) (CNCM I-2433). The weight ratio of Enzyme: Lactic acid bacteria is preferably from about 1:1 to about 4:1 based on % (w/w) addition of the ingredients.

The hydrolysis may be carried out for a time sufficient for the LAB to produce 1 to 4 % MSG in the hydrolysate or to have a DH of at least 20%. The hydrolysis of the protein-containing material is thus preferably carried out at a temperature of at least about 30–50° C. The pH is preferably maintained between about 5 to 6. The reaction may be carried out for at least 12 hours.

The hydrolysate may be further processed downstream by means of thermal inactivation, filtration and/or centrifugation to produce a raw sauce. In a preferred embodiment, the hydrolysate is pasteurized, salt is added and the hydrolysate is filtered to separate solids from the liquid phase.

The process according to the present invention has numerous advantages. It efficiently competes spoilage micro-organisms, like coliform bacteria. It is entirely biological and good hydrolysis of the protein material is obtained. Moreover, it is shorter than any process for biological hydrolysates described up to date.

Furthermore the above mentioned process employs synergistic effects of added enzymes (proteases, peptidases) and enzymes provided by the lactic acid bacteria. Compared to similar hydrolysates, produced by enzymes only, the cultured hydrolysates show an increased DH and an increased yield of MSG.

The present invention also relates to an isolated thermo-tolerant LAB strains selected for their ability to provide a glutaminase activity. The selected strain can eliminate reducing sugars such as glucose and maltose. The LAB strain may also provide increased release of proline from peptide bonds.

In a preferred embodiment, the LAB strain is selected from the group consisting of facultative heterofermentative

*Lactobacilli*, *Lactobacillus rhamnosus*, *Lactobacillus delbrucki*, *Lactobacillus casei*, *Lactobacillus paracasei*, and *Lactobacillus* sp. In a most preferred embodiment the LAB strain is *Lactobacillus rhamnosus* (NCC 858) (CNCM I-2433).

In another aspect, the invention relates to the use of thermotolerant LAB strains having the above traits as process micro-organisms for the preparation of seasonings. The strains according to the present invention provide a microbiological protection of the process and a significant elimination of the reducing sugars leading to decreased uncontrolled Maillard reactions, which improves the shelf-live stability and applicability of the product. Moreover, the selected strains do not impair the body-giving and taste characteristics of the hydrolysate and even contribute to an improved body and taste (higher degree of hydrolysis, higher MSG yield).

DETAILED DESCRIPTION OF THE PREFERRED EMBODIMENTS

Within the following description, the abbreviation cfu ("colony-forming-unit") designates the number of bacterial cells as revealed by microbiological counts on agar plates.

In the specification, all percentages are given on the basis of weight except where specifically stated otherwise.

As quality marker to monitor the efficiency of protein hydrolysis, the DH is formulated as follows: DH=("conc. of free N$\alpha$"×100)/"conc. of total nitrogen".

Moreover, "NCC" designates Nestlé Culture Collection (Nestlé Research Center, Vers-chez-les-Blanc, Lausanne, Switzerland).

The protein containing material is preferably obtained from plant or animal origin. Plant protein material may be wheat gluten, defatted soya-grits, defatted soya beans, corn gluten, rice gluten, sun flower presscake, for example. It more preferably is wheat gluten. Animal protein material such as milk proteins, chicken meal, beef or pork, for example, may also be used as substrate for the present process. The protein containing material is preferably used in a dry, powdered form, or as grits.

The protein containing material is preferably mixed with water so as to obtain a porridge/slurry. The resulting slurry is then subjected to a hydrolysis by using a combination of at least one enzyme with at least one thermotolerant lactic acid bacteria strain selected for its ability to provide a glutaminase activity.

The enzyme according to the present invention may be any endo- or exo-peptidase, deaminase, transaminase, glutaminase or amyloglucosidase, for example. It is preferably used Flavorzyme®, Alcalase®, Dextrozyme®, AMG®. These enzymes were provided by Novo Nordisk Ferment AG, Dittigen, Switzerland. The enzyme may be used alone or in combination. The enzyme may be used in an amount which can vary according to the enzyme used. If a protease is used, the amount is preferably of at least 0.2% by weight based on the total reaction and preferably from about 1% to about 4%. If a technical carbohydrase is used, the amount is preferably of about at least 0.05% by weight based on the total reaction.

At least one thermotolerant lactic acid bacteria (LAB) strain is used in combination with the enzyme. The lactic acid bacteria strain has the traits as further described. It may be selected from the group consisting of facultative heterofermentative *Lactobacilli*, *Lactobacillus delbrueckii*, *Lactobacillus casei*, *Lactobacillus paracasei* and *Lactobacillus rhamnosus* and is most preferably *Lactobacillus rhamnosus* (NCC 858)(CNCM I-2433).

The selected lactic acid bacteria strain is advantageously added in the form of a starter resulting in a titer of about $10^4$ to about $10^7$ cfu/g in the hydrolysate at the start of the reaction. The starter may be added to the hydrolysate reaction in an amount of at least 0.1% (v/v) and preferably from about 0.5 to 2% (v/v) or so that the amount in the hydrolysate reaction at the start is preferably of about $5\times10^5$ to about $2\times10^6$ cfu/g.

The ratio enzyme: lactic acid bacteria is preferably of about 1:1 to about 4:1 based on % (w/w) addition of the ingredients.

In a preferred embodiment the present process is carried out by hydrolyzing the protein containing material, by mixing 15 to 30% of the protein containing material in 65 to 80% water to obtain a slurry, then adding to the slurry about 0.2% to about 0.88% (based on the total reaction) of at least one enzyme and about 0.1% to about 1% of a starter (an inoculum) of at least one lactic acid bacteria strain having a titer of about $10^{9-1011}$ cfu/g (in the concentrated starter culture). The percentages are given by weight based on the total reaction.

The hydrolysis of the protein-containing material may be carried out at a temperature of at least 43° C., and preferably from about 45 to about 48° C. The pH may be of about 5 to 6. The pH can be maintained by adding acetate buffer pH 5.8 or calcium carbonate, for example.

The hydrolysis is preferably carried out for a time sufficient for the lactic bacteria strain to grow by 2–3 log, or to create 1–4% mono-sodium glutamate or glutamic acid in the hydrolysate, or to have a degree of hydrolysis (DH) of at least 20%.

In a preferred embodiment, the hydrolysis may be carried out for at least 12 hours, and most preferably from about 15 to about 24 hours.

During this protein hydrolysis reducing sugars are released, due to enzymatic side activities in the enzyme preparations. The reducing sugars are reaction partners in Maillard reactions and can thus cause browning and the creation of bitter notes during storage. The selected lactic acid bacteria which is thermotolerant, eliminates glucose and maltose, but does not impair the function of the enzymes or produce off-flavors. Due to the elimination of the sugars, the lactic acid bacteria strain will also function as a protective culture and has antimicrobial activity against gram$^-$and gram$^+$bacteria. The obtained hydrolysate is then low in reducing sugars. Glucose can be eliminated completely during the hydrolysis, while the maltose concentration may be partly reduced.

Then, the hydrolysate may be treated in different ways in order to prepare a liquid, a paste or a powder as is conventionally known.

In a preferred embodiment, the hydrolysate is dried (vacuum drying at 60–90° C. at about 15 to 4 mbar for 3hrs, spray drying in Niro spray dryer at an inlet air temperature of 140° C.–180° C. and outlet air temperature of about 90° C., at about 1600 UpM.) so as to obtain a powder with a dry matter content of at least 98%. Alternatively the hydrolysate can be concentrated for use in liquid seasoning. The obtained savory base may be use in liquid seasoning applications, for example.

In another embodiment, up to 15% NaCl can be added after the hydrolysis, and the hydrolysate is heated up to about 90° C. and kept at this temperature for about 10 minutes to inactivate enzymes and microbial metabolic activity (pasteurization).

In another embodiment, the inactivated hydrolys ate is cooled down and kept at about 55° C. and then filtered either through plate and frame filters or alternatively by using a Hoesch filter press. After filtration a cleared raw sauce with a TS of 30–35% is obtained.

In order to stabilize the raw sauce even further, it can be reacted by incorporating cysteine in an amount of from 0.01 to 0.1 part by weight and then heat treating the mixture at 95° C. to 110° C. for 1 to 5 hours, as described in U.S. Pat. No. 5,480,663.

The cultured hydrolysis produces hydrolysates with a good round body (mouthfeel) and neutral taste with good body-giving potential and with a decreased content of reducing sugars.

Furthermore, low levels of reducing sugars lead to decreased uncontrolled Maillard reactions, which improves the shelf-live stability of the product.

Hydrolysates were prepared by using enzymes only. It has been shown that such hydrolysates contain higher concentrations of reducing substances and lacks lactate, which is produced during cultured hydrolysis. The cultured hydrolysates according to the present invention show an increased degree of hydrolysis and an increased yield of MSG. The cultured protein hydrolysis process appears to be a self-regulating system, where the parameters enzyme concentration, inoculum dosage, metabolic activity of the micro-organism, pH of the reaction and temperature are in a dynamic equilibrium with each other.

The hydrolysates according to the present invention are good candidates for body givers in process flavors and culinary applications, as shown in the following examples.

In a preferred embodiment, the cultured hydrolysate is used directly in its liquid or dried form so as to enhance or impart a savory type flavor in culinary products, for example. The amount of the liquid form is preferably of about 0.05 to 750 g per kg of culinary product or petfood product, depending on the required aroma intensity. The dried form of the flavoring agent can be used in an amount of 0.2–250 g per kg product.

According to another object of the present invention, several strains of thermotolerant lactic acid bacteria (LAB) were screened according to their properties and physical parameters: food grade and having GRAS status, capability to metabolize both glucose and maltose, thermotolerance between 40° C. and 55° C.

The selected LAB strains are food-grade. They are thermotolerant (i.e., growth between 40° C.–48° C.) and growth on/isolation from plants. They also have the ability to metabolize glucose and maltose. They do not impair the function of the enzymes, the body-giving and taste characteristics of the hydrolysate and do not produce off-flavors.

In a preferred embodiment, the LAB is selected from the group consisting of facultative heterofermentative *Lactobacilli, Lactobacillus rhamnosus, Lactobacillus delbrueckii, Lactobacillus casei, Lactobacillus paracasei* and other *Lactobacillus* sp, for example.

In a more preferred embodiment, the LAB is *Lactobacillus rhamnosus* NCC 858 (CNCM I-2433).

The *Lactobacillus rhamnosus* (NCC 858) strain was deposited by way of example under the Budapest Treaty at the Collection Nationale de Cultures de Microorganismes (CNCM), Institut Pasteur, 28 rue du Docteur Roux, 75724 Paris Cedex 15, France, on Apr. 5, 2000, under the reference CNCM I-2433.

Biochemical Characterization of the Selected Strain
*Lactobacillus rhamnosus* (NCC 858)

Gram positive microorganism, non motile, non sporulating.

Rod shaped cells; 0.8–1 μm by 2–4 μm, often with square ends, occur singly or in short chains.

Microaerophilic micro-organism with facultative heterofermentative metabolism, production of L(+) lactic acid.

Catalase negative, production of $CO_2$ facultative

Fermentation of the sugars: Amygdaline (+), Arabinose (+/–), Cellobiose (+), Esculin (+), Gluconate (+), Mannitol (+), Melecitose (+), Melibiose (–), Raffinose (–), Ribose (+), Sorbitol (+), Sucrose (+), Xylose (+).

Growth up to 48° C. possible.

In another embodiment, the invention relates to the use of thermotolerant lactic acid bacteria (LAB) strains having the above traits as process micro-organisms for the preparation of seasonings. The selected LAB may be used in a process for preparing savory bases as described above, for example. Surprisingly it was found that culturing using *Lactobacillus rhamnosus* NCC 858, for example, could eliminate the use of technical glutaminase for conversion of glutamine to glutamate. Additionally NCC 858 also show some proteolytic activity.

The LAB strains according to the present invention do not impair the body-giving and taste characteristics of the hydrolysate and even contribute to an improved body and taste (higher degree of hydrolysis, higher MSG yield). The LAB strains may also provide a microbiological protection of the flavoring process and a significant elimination of the reducing sugars leading to decreased uncontrolled Maillard reactions, which improves the shelf-live stability of the product.

EXAMPLES

The following examples are given by way of illustration only and in no way should be construed as limiting the subject matter of the present application.

Example 1

Strain NCC 858 was used for the initial experiments to set up suitable reaction conditions. For the initial trials the pH of the reaction was maintained at 5.8 by dosing NaOH to the system. The reactions were based on the following recipe:

| Ingredients | % (w/w) based on total reaction |
|---|---|
| Wheat gluten | 22 |
| Water | 75 |
| Flavorzyme ® (based on wheat gluten) | 1 |
| Glutaminase C200 ® (based on wheat gluten) | 0.5 |
| Acetate buffer pH 5.8 | 0.25 |
| LAB starter | 5e5 cfu/g |

Table 1 summarizes the results of the growth test with NCC 858, to find the optimal growth and reaction temperature in the cWGH-te process.

TABLE 1

Growth test in cultured process medium

| Temp[1]. | Cfu/g[2] [0 h] | Cfu/g[2] [16 h] | RS[3] [0 h] | RS[3] [16 h] | DH[4] [16] |
|---|---|---|---|---|---|
| 45° C. | 1 E6 | 1.5 E9 | Glc 0.3% Mal 1% | Glc <0.05% Mal 0.3% | 23–27% |
| 55° C. | 1 E6 | 3 E2 | Glc 0.3% Mal 1% | Glc 0.48% Mal 1.2% | 23–26% |

[1]Temperature of hydrolysis reaction,
[2]indicated are the counts for NCC 858 in the hydrolysate at the start. For coliforms, bacilli, spores the counts were <10 cfu/g after 16 h,
[3]reducing sugars,
[4]degree of hydrolysis as ratio between free amino acids and total nitrogen concentration.

The results clearly show (cfu and sugar concentrations) that at 45° C. there is good growth of the micro-organism during the 16 h of hydrolysis. Subsequent hydrolyses have though shown that temperatures up to 47° C. are tolerated by strain NCC 858. Monitoring of the degree of hydrolysis shows that the efficiency of hydrolysis of the enzymes is as efficient at 45° C., as it is at 55° C.

Determination of Possible Dosage Range for NCC 858 Starter in cWGH-te Process

It has been shown, that a dosage range for the inoculi between 1 E4 cfu/g and 1 E6 cfu/g does not have a negative influence on the hydrolysis. An inoculum of 5 E7 is too high, the yields for the quality markers MSG and free alpha amino-nitrogen sink significantly.

Microbiological monitoring for coliforms, AMC and AMS showed that there was good protection exerted by NCC 858 in the entire dosage range. Dosages lower than 1 E4 cfu/g were not tried, in these cases the inoculum can no more dominate the contaminating flora present in the raw material.

Evaluation of the Effect of Enzyme Dosage on the Cultured Hydrolysis Process

It was also tested different concentrations of Flavorzyme® and Glutaminase to determine where the optimum will be with respect to enzyme applied/costs and increase in the yield of the quality markers (Nα and MSG).

For all experiments the pH was left free. The dosage of the inoculum was 1E5 cfu/g.

Different concentrations of enzymes were used for the preparation of a cultured wheat gluten hydrolysate (cWGH-te) and the results were compared with a process using different concentrations of enzymes alone (WGH-te). The results are given in Table 2.

TABLE 2

Comparison of analytical results for process using different concentrations of enzymes (cWGH-te and WGH-te)

| Conditions | Trial | MSG[5] | DH[1] | Glc[3]/Mal[4] | RS[2] | Dry |
|---|---|---|---|---|---|---|
| 1% Flav, 0.5% Gln, 0.1% Alc | CWGH-WGH-te | 1.94 1.89 | 28.1 24.3 | 0.05/0.93 n.a./n.a. | 1.12 1.66 | 31.7 32.9 |
| 2% Flav, 0.5% Gln, 0.1% Alc | CWGH-WGH-te | 2.46 2.16 | 32.3 26.8 | 0.098/0.56 n.a./n.a. | 1.37 1.93 | 32.2 33 |

[1]degree of hydrolysis as defined,
[2]Reducing substances (sugars and others),
[3]Glucose,
[4]Maltose
[5]Mono sodium glutamate, Flav: Flavorzyme ®; Gln: Glutaminase; Alc: Alcalase ®

The results show that in the cultured samples the concentration of the quality markers are higher compared to the corresponding versions with enzymes only. Especially with respect to the DH, the difference between the cultured and non-cultured hydrolysates are remarkable. For both the enzyme—and the cultured versions the most significant increase in the concentration of the quality marker MSG occurs in the step from 1% to 2% Flavorzyme®. An increase of the glutaminase concentration by 50% (0.5 to 0.75%) at each respective Flavorzyme® concentration results in a moderate increase of the MSG concentration.

For the MSG yield: Significant yield increases are seen in dependence of the Flavorzymeg dosage. The increase of glutaminase dosage by 50% at a given Flavorzyme® concentration is only marginal. This could thus indicate that the release of glutamine is rate limiting, rather than the glutaminase action. Furthermore, the higher MSG yields in the cultured hydrolysates compared to the corresponding "enzyme hydrolysates" gives indications that the process micro-organism *L. rhamnosus* contributes a "glutaminase activity". The higher degree in hydrolysis in the cultured versions argues further that *L. rhamnosus* contributes also to the proteolytic activity in the hydrolysis.

The comparison within the samples produced with "enzymes only" shows: There is a clear dependence on the enzyme dosage for both, the increase in the degree of hydrolysis (yield of free amino acids) and the increase in MSG yield.

The increase in the degree of hydrolysis is more pronounced than the one for the MSG yield, again indicating that the release of glutamine is the rate limiting step.

It was then determined if the cultured hydrolysis process can be run without addition of glutaminase.

Cultured Hydrolysis Process with Flavorzyme®/Alcalase® as Only Enzymes

The dosage range of 1–3% Flavorzyme® was tested in this series. Alcalase® was added to 0.1% in all trials. The recipe for the hydrolysates is otherwise identical to the one already described above.

Table 3 shows the comparison of the analytical values for the above quoted trials, the enzyme versions WGH-te (2% Flavorzyme®, 0.1% Alcalase®) and WGH-te (4% Flavorzyme®D, 1% GlutaminaseC200®, 0.1% Alcalase®) were used for comparison.

TABLE 3

Comparison of analytical results for the process using Flavorzyme ®/ Alcalase ® as only enzymes at different dosages.

| | Dosage of Inoculum | Enzyme | [% w/w] | | | | |
|---|---|---|---|---|---|---|---|
| | cfu/g | conc. | MSG[5] | DH[1] | Glc[3]/Mal[4] | RS[2] | DM |
| WGH-te | No | 2% Flav, 0.1% Alc | 0.27 | 24.55 | n.a./n.a. | 1.83 | 32.9 |
| cWGH-te | 2 E5 | 0.1% Alc | 2.67 | 32.71 | 0.05/0.72 | 1.02 | 32.3 |
| cWGH-te | 5E5–1E6 | | 2.49 | 30.6 | 0/0.67 | 0.93 | 32.3 |
| cWGH-te | 2 E6 | 1% Flav, 0.1% Alc | 1.34 | 22.96 | 0.05/0.69 | 0.93 | 31.4 |
| cWGH-te | 2 E6 | 3% Flav 0.1% Alc | 2.9 | 33.04 | 0/0.58 | 1.05 | 33.4 |
| WGH-te | No | 4% Flav, 1% Gln, 0.1% Alc | 3.2 | 35.7 | n.a./n.a. | 2.24 | 29.7 |

[1]degree of hydrolysis as defined
[2]Reducing substances (sugars and others),
[3]Glucose,
[4]Maltose,
[5]Mono sodium glutamate, Flav: Flavorzyme ®, Gln: Glutaminase, Alc: Alcalase ®.

The data in Table 2 show clearly that hydrolysates made with only 2% Flavorzyme(®) and NCC 858 starter only, produce good levels of the quality markers MSG and DH. The data in Table 3 shows that the same levels of the quality markers MSG and DH are obtained with such hydrolysates as those made with 2% Flavorzyme® and 0.75% technical glutaminase (Glutaminase C200®) (see cWGH-te row 7 in Table 3). In other words, the addition of technical glutaminase does not improve the MSG yield or the degree of hydrolysis in the cultured process.

Processing using only Alcalase(®) and L. rhamnosus NCC 858 or NCC 858 alone, only result in low DH ($\leq 15\%$) and low yields of MSG ($\leq 0.5\%$). The action of Flavorzyme® on the substrate and potentially also on the process microorganism are preferably needed to produce a good quality hydrolysate. The action of Flavorzyme® on the process microorganism has been deduced from physiological analysis of the cells at the end of the hydrolysis before inactivation (swelling).

Example 2

Preparation of a Savory Base (or Dried Cultured Hydrolysate)

In order to prepare a cultured wheat gluten hydrolysate, 22% of wheat gluten is mixed in 75% of water to obtain a slurry. The obtained slurry is then hydrolyzed, by adding 1% Flavorzyme® (based on wheat gluten) and 0.1% of Alcalase® and 1% of a starter of Lactobacillus rhamnosus (NCC 858) (CNCM I-2433) having a titer of $5 \times 10^5$ cfu/g.

The pH for the hydrolysis is maintained at about 5.8 by adding 0.25% of acetate buffer pH 5.8 and the reaction is carried out at 45–48° C. during 16 hours so as to obtain the cultured hydrolysate.

Then, the hydrolysate is vacuum dried at 66° C. at about 15 to 4 mbar for 3 hours so as to obtain a powder. The powder has a dry matter content of at least 98%. This powder may be used as in Example 5.

Alternatively the hydrolysate can be concentrated to a dry matter of about 35% for use in liquid seasoning as in Example 4.

Example 3

Preparation of a Raw Sauce (Liquid Savory Base)

A cultured hydrolysate is prepared as described in Example 2. After the hydrolysis 15% of NaCl is added. The hydrolysate is then heated up to about 90° C. and kept at this temperature for about 10 minutes to inactivate enzymes and microbial metabolic activity (pasteurization).

The inactivated hydrolysate is cooled down and kept at about 55° C. and then filtered by using a Hoesch filter press. After filtration a cleared raw sauce with a TS of 30–35% is obtained. This raw sauce may be utilized for the preparation of seasonings (cf Example 4).

The raw sauce can also be evaporated and vacuum dried and then milled into a powder. This powder can the be used in culinary and flavor applications as demonstrated in Examples 5 and 6.

Example 4

Liquid Seasoning

In order to prepare a liquid seasoning, the following ingredients are mixed together in a stirred reactor:

| Ingredient | [%] |
|---|---|
| cWGH-te powder as prepared in Example 2 | 75.0 |
| Water | 13.5 |
| Salt | 5.5 |
| Lovage flavor | 5.0 |
| MSG | 3.5 |
| Caramel color | 0.5 |

The mixture is then pasteurized at a temperature of 95° C. during 15 minutes and, subsequently the seasoning is transferred into brown bottles for storage and application tests.

Example 5

Application in a Culinary Product (Soup)

This example demonstrates the use of the cultured hydrolysate powder prepared as in Example 2, as a flavor ingredient for a culinary application (mushroom soup). The soup has the following composition:

| Ingredient | [%] |
|---|---|
| Onion powder | 0.5 |
| cWGH-te powder | 3.0 |
| Modified starch | 12.0 |
| Skim milk powder | 10.8 |
| Wheat flour | 12.0 |
| MSG | 5.3 |
| Salt | 7.7 |
| Mushroom powder | 6.0 |
| Non-milk fat creamer | 10.6 |
| Maltodextrin | 17.0 |
| Fat | 11 |

All the ingredients are mixed together in a conventional mixer. The soup is a dry culinary powder. 100 g of powder are mixed with 800 ml of water and 200 ml partially skimmed milk and cooked for 5minutes (simmering).

Example 6

Taste Testing of Raw Sauce and Dried powder

Raw sauce, as prepared in Example 3, is mixed with water (80° C.) at a dosage of 10 g/l. These samples were then tasted by a random panel of collaborators ($\geq 4$ persons) and assessed for the following descriptors: smell, taste, body, color and rating (compared to standard samples). Table 4 shows the hydrolysates tasted and the general comments of the taste panel to the different products.

TABLE 4

Technical taste testing of WGH-te and cWGH-te samples

| Trial | Product | Assessment |
|---|---|---|
| I | 1% Flav 0.5% Gln Starter titer 1e4 | Body is present, but needs to be stronger. Slight acidity is perceptible, different tasters react differently to it No fermentation off-note slightly turbid |
| II | 1% Flav 0.5% Gln | Body weaker than in I. |

TABLE 4-continued

Technical taste testing of WGH-te and cWGH-te samples

| Trial | Product | Assessment |
|---|---|---|
| III | 4% Flav, 0.75% Gln, 0.1% Alc Starter titer 1e5 | Strong body<br>Acidity is present<br>roasty notes are perceptible (from drying of the powder)<br>less neutral than other cultured hydrolysates samples<br>slight fermentation off-note |
| IV | 2% Flav 0.1% Alc Starter titer 2e5 | Good, strong body and round taste<br>Acidity is perceptible, different tasters react differently to it<br>No fermentation off-note, neutral |
| VI | 2% Flav 0.1% Alc | Much weaker body than IV and V. |
| VII | 4% Flav 1% Gln 0.1% Alc | Good strong body, round and neutral taste<br>No acidity<br>No fermented off-notes |

Flav: Flavorzyme ®,
Gln: Glutaminase,
Alc: Alcalase ®,
Starter: *Lactobacillus rhamnosus* NCC 858

NCC 858

The technical taste testing showed that the cultured versions using 2% Flavorzyme® have been judged as very interesting for trials in process flavors.

Example 7

Petfood Composition

A mixture is prepared from 70% of poultry carcass, pig lungs and beef liver (ground), 18% of wheat flour, 8% of water, and 0.2% of liquid cultured hydrolysate as prepared in Example 2, vitamins and inorganic salts.

This mixture is emulsified at 12° C. and extruded in the form of a pudding which is then cooked at a temperature of 90° C. It is cooled to 30° C. and cut in chunks. 45% of these game flavored chunks are mixed with 55% of a sauce prepared from 98% of water, 1% of dye and 1% of guar gum. Tinplate cans are filled and sterilized at 125° C. for 40 min.

This petfood has a pleasant flavor as perceived by smelling the sample.

What is claimed is:

1. A process for the preparation of a cultured savory base, which comprises hydrolyzing, for a sufficient time to prepare a savory material, a protein-containing material using a combination of at least one enzyme with at least one thermotolerant lactic acid bacteria strain selected for its ability to provide a glutaminase activity such that the base maintains glutaminase activity in order to provide glutamic acid or a glutamate in the base in an amount sufficient to enhance body and taste.

2. A process according to claim 1, wherein the hydrolysate of savory material is further processed by thermal inactivation, filtration or centrifugation to produce a raw sauce.

3. A process according to claim 1, wherein the protein-containing material is of plant or animal origin.

4. A process according to claim 3, wherein the protein-containing material is wheat gluten, rice protein, soya, corn gluten, sunflower presscake, milk protein or animal protein.

5. A process according to claim 1, wherein the ratio enzyme: lactic acid bacteria strain is of about 1:1 to 4:1 based on % (w/w) addition of those ingredients.

6. A process according to claim 1, wherein the enzyme is an exo- or endo-protease, deaminase, carbohydrase or amyloglucosidase.

7. A process according to claim 1, wherein the enzyme is used in an amount of at least 0.2% (protease) or 0.05% (carbohydrase) by weight based on the total reaction.

8. A process according to claim 1, wherein the thermotolerant lactic acid bacteria is selected from the group consisting of facultative heterofermentative *Lactobacilli, Lactobacillus rhamnosus, Lactobacillus delbrucki, Lactobacillus casei, Lactobacillus paracasei* and *Lactobacillus* sp.

9. A process according to claim 1, wherein the lactic acid bacteria is *Lactobacillus rhamnosus* (NCC 858) CNCM I-2433.

10. A process according to claim 1, wherein the lactic acid bacteria is added in the form of a starter having a titer of about 1E9–1E11 cfu/g, in an amount of at least 0.1 to 0.5 % (w/w).

11. A process according to claim 1, wherein the hydrolysis is carried out for a time sufficient for the lactic bacteria strain to grow by 2–3 log, or to create 1–4% mono-sodium glutamate in the hydrolysate, or to have a degree of hydrolysis of at least 20%.

12. A process according to claim 1, wherein the hydrolysis is carried out at 43° C.–48° C., at pH 5–6 for a time of at least 12 hours.

13. A process according to claim 1, wherein a slurry containing 15 to 30% of the protein containing material and 65 to 80% of water, is hydrolyzed using 1 to 4% of at least one enzyme combined with 0.5 to 2% of a lactic acid bacteria starter having a titer of about 1E5–1E6 cfu/g, in an amount of at least 01. to 0.5% (w/w).

14. An isolated thermotolerant lactic acid bacteria strain selected for its ability to provide a glutaminase activity in order to provide glutamic acid or a glutamate.

15. The isolated strain according to claim 14, which is selected from the group consisting of facultative heterofermentative *Lactobacilli, Lactobacillus delbrueckii, Lactobacillus casei, Lactobacillus paracasei* and *Lactobacillus rhamnosus*.

16. The isolated strain according to claim 14, which is *Lactobacillus rhamnosus* (NCC 858) CNCM I-1-2433.

17. A method for preparing a seasoning or flavor for a culinary or petfood product which comprises treating a protein material with the isolated strain of lactic acid bacteria according to claim 14 for a time and under conditions sufficient to form a savory material.

18. The method of claim 17, wherein the protein material is hydrolyzed with the bacteria in combination with at least one enzyme.

19. The method according to claim 18, wherein the enzyme and lactic acid bacteria strain are used in relative amounts to provide a ratio of enzyme: lactic acid bacteria strain of about 1:1 to 4:1 based on % (w/w) addition of those ingredients.

* * * * *